(12) United States Patent
Feeser et al.

(10) Patent No.: US 6,517,547 B1
(45) Date of Patent: Feb. 11, 2003

(54) STENT DELIVERY SYSTEM

(75) Inventors: Joerg Feeser, Koenigsbach-Stein; Lars Schendzielorz, Linkenheim-Hochstetten, both of (DE)

(73) Assignee: Angiomed GmbH & Co. Medizintechnik KG, Karlsruhe (DE)

(*) Notice: Subject to any disclaimer, the term of this patent is extended or adjusted under 35 U.S.C. 154(b) by 0 days.

(21) Appl. No.: 09/637,617

(22) Filed: Aug. 11, 2000

(30) Foreign Application Priority Data

Sep. 7, 1999 (DE) .................................. 299 15 724 U

(51) Int. Cl.⁷ .................................................. A61F 11/00
(52) U.S. Cl. ........................................ 606/108; 606/198
(58) Field of Search .......................... 606/108, 191, 606/198, 194, 195, 192; 623/1.11

(56) References Cited

U.S. PATENT DOCUMENTS

| 5,064,435 | A |   | 11/1991 | Porter |
| 5,645,559 | A |   | 7/1997  | Hachtman et al. |
| 5,690,644 | A | * | 11/1997 | Yurek et al. ............... 606/108 |
| 5,817,102 | A |   | 10/1998 | Johnson et al. |
| 5,944,726 | A |   | 8/1999  | Blaeser et al. |
| 5,968,052 | A | * | 10/1999 | Sullivan, III et al. ....... 606/108 |

FOREIGN PATENT DOCUMENTS

| DE | 3713384 C2 | 2/1995 |
| DE | 4333836 A1 | 4/1995 |
| EP | 0274846 A1 | 7/1988 |
| EP | 0540290 A2 | 5/1993 |
| EP | 0556850 A1 | 8/1993 |
| EP | 0587197 A1 | 3/1994 |
| EP | 0647438 A1 | 4/1995 |
| EP | 0761251 A1 | 3/1997 |
| EP | 0775470    | 5/1997 |
| WO | WO 91/12779 | 9/1991 |
| WO | WO 93/17636 | 9/1993 |
| WO | WO 94/17754 | 8/1994 |
| WO | WO 9947075  | 9/1999 |

* cited by examiner

*Primary Examiner*—Kevin T. Truong
(74) *Attorney, Agent, or Firm*—Kirkpatrick & Lockhart LLP

(57) ABSTRACT

The present invention relates to a stent delivery system comprising a catheter tube defining for a self-expanding stent a bed having a length direction in line with the catheter length, a radially outward facing stent-receiving surface, a distal end at or near the distal end of the catheter and a proximal end spaced proximally from the distal end; an outer catheter tube to circumferentially surround the bed; and the outer tube being arranged to be withdrawn proximally to release the self-expanding stent radially outwardly from the bed; and further comprising: on the stent receiving bed surface, immediately distal of the proximal end of the bed, a first pinch zone; on the outer tube, at or near a distal end thereof, and on its radially inwardly facing surface, a second pinch zone; the first and second pinch zones facing each other when the distal end of the outer tube is not quite fully withdrawn proximally, relative to the bed; the facing of the opposed first and second pinch zones defining a reduced-width annulus for pinching the proximal end of the stent to make available increased resistance to relative axial movement between the stent and the catheter shaft just prior to full withdrawal of the outer tube.

18 Claims, 1 Drawing Sheet

STENT DELIVERY SYSTEM

BACKGROUND OF THE INVENTION

1) Field of the Invention

In the context of this specification, a stent is a support structure, more or less tubular, for placement within a bodily lumen to support the tissue walls of the lumen. These stents usually require a delivery system to bring them to precisely the desired position within the body of the patient. This invention relates to stent delivery systems.

Two broad categories of stent can be identified. In one category, the stent is fitted around a sausage-shaped balloon, the balloon itself being on the distal end of a catheter. The catheter is advanced, for example, in the arterial system of the patient to the location where the stent is to be placed, and the balloon is then inflated to deform the stent plastically, expanding the stent radially against the wall of the bodily lumen. Since the deformation is plastic, the stent remains in its expanded disposition after deflation of the balloon, and the catheter and balloon system can then be withdrawn.

A second category of stent comprises stents which are self-expanding. For these stents, the delivery system employs some sort of sheath to constrain the stent in a radially small configuration. When the stent is in the desired location, the constraint radially outside the stent is withdrawn, allowing the stent to "spring" radially outwardly to press against the tissue wall of the lumen and permit withdrawal of the delivery system.

The present invention relates to a delivery system for a self-expanding stent. In this specification, the expression "proximal" relates to a point at the end of the delivery system held by the physician, and "distal" to the opposite end.

2. Description of the Related Art

U.S. Pat. No. 5,645,559 (Hachtman et al.) discloses a delivery system for a radially self-expanding stent, the system having an inner tube around which the stent is fitted, and an outer tube that radially compresses the stent. FIGS. 5 to 8 of the drawings of US'559 shows progressive proximal withdrawal of the outer tube so as to release the self-expanding stent progressively along its length commencing with the distal end, and with the extreme proximal end of the stent being the last part of the stent to be released radially outwardly.

US'559 mentions the problem that during this release process there have been instances of axial travel of the stent relative to the delivery system, and not under the control of the surgeon or radiologist, so that the stent can end up in a position in the bodily lumen either proximal of or distal of, the desired location in the lumen. US'559 addresses this problem and proposes as a solution the addition of a relatively soft sleeve element which sits between the stent and the inner tube. This soft sleeve is required to exhibit on its radially outward surface a plurality of circumferential ribs. US'559 stresses that the ribs should be adjacent to the medial portion of the stent. Its FIG. 22 shows a bed 21 for the stent and what appear to be 14 ribs all in the central part of the length of the bed.

SUMMARY OF THE INVENTION

The present invention also addresses the problem of uncontrolled movement of a self-expanding stent relative to a stent delivery system, during the process of deploying the stent. The features which characterize the present invention are recited in claim 1 below. The dependent claims recite optional or preferred features.

The technical features of the present invention deliver an improved technical effect. The degree to which a self-expanding stent is gripped by a stent delivery system involves a judicious balance between different factors, and the present invention offers the possibility of a better balance, as follows.

Unwanted jumping of the stent out of the delivery system can be combated by providing a tight fit between the constraining surfaces inside and outside the stent. In other words, one can confine the stent in a very tight annular space, giving the stent minimal opportunity to spring out of the annular space prematurely. However, it is also important to ensure that, when release of the stent is desired, release can proceed smoothly. For this purpose, one would choose to have easy axial sliding between the constraining surfaces inside and outside the stent cylinder. In other words, it must be possible easily to proximally withdraw the outer constraining sheath. This factor points towards a loose fit of the sheath on the stent.

One insight which the present inventor has brought to this complex is the realization that the grip of the delivery system on the stent gets weaker as the sheath progressively withdraws since the area of sheath overlying the compressed part of the length of the stent is progressively shrinking. Thus, the likelihood of an uncontrolled spring of the stent away from the delivery system goes up in proportion to the amount of proximal withdrawal of the sheath. Thus, as long as the sheath grips tightly the proximal end of the stent in the last stages of stent release a looser grip on the distal end of the stent, in the early stages of release, is likely to be tolerable. If one assumes that resistance to proximal withdrawal of the sheath will be in proportion to the surface area of the sheath in sliding contact with the radially outside surface of the stent, then one can appreciate that the force required to pull the sheath proximally will tend to ease downwards, as the sheath progressively withdraws from the stent surface.

According to the present invention, pinch zones interact in the last stages of sheath withdrawal. This raises frictional resistance, but from a low level. The pinching effect enhances gripping of the stent when enhanced gripping is needed, however not before then.

With the invention, it will be noted, there is no interaction of the pinch zone on the sheath and the pinch zone on the catheter until after a majority of the length of the stent has already been released. Thus, the pinch zones do not materially add to the sliding resistance during release of the stent, until the last part of the release process. During this last part of the release process, the amount of sliding resistance is less than the frictional resistance at the start of the release process so that there is some scope for a tighter squeezing of the proximal end of the stent between two annular surfaces, without taking the frictional resistance back up to an unacceptably high level. Indeed, a judicious balance of materials and dimensions should enable a profiling of the frictional resistance so that the interaction between the first and second pinch zones compensates for the decline of frictional resistance with proximal movement of the sleeve, possibly leading to a more or less steady level of force needed for withdrawal of the sheath over the full length of the stent. Alternatively, the profile could be arranged to provide a signal, in terms of a characteristic tensile stress profile, delivered to the surgeon/radiologist that the second pinch zone has passed over the first pinch zone.

It is conventional in stent delivery systems to equip the delivery system with radioactive markers to enable radiologists to track the location of the distal end of the system. Often, the catheter is fitted with distal and proximal markers, of known disposition relative to the stent bed, and the constraining sheath also has a marker so that the degree of withdrawal of the sheath, relative to the stent bed, can also be tracked. Conveniently, these radioactive markers are thin metal bands crimped or swaged onto the outside surface of a polymeric tubular element. In one preferred embodiment of the present invention, such a metal radioactive marker band is fitted around the sheath at its distal end, and squeezed into the outside wall of the sheath by an amount calculated to displace the sheath wall, inside the marker band just enough to create the second pinch zone.

One convenient way to create the first pinch zone is by depositing on the cylindrical wall of a tube of the catheter an annulus of cured polymeric adhesive. Preferably, a metal radioactive marker band can be set within the same adhesive deposit, thereby to form the proximal end of the stent bed.

BRIEF DESCRIPTION OF THE DRAWINGS

For a better understanding of the present invention, and to show more clearly how the same may be carried into effect, reference will now be made, by way of example, to the accompanying drawings, in which.

DETAILED DESCRIPTION OF THE PREFERRED EMBODIMENT

Figure 1:
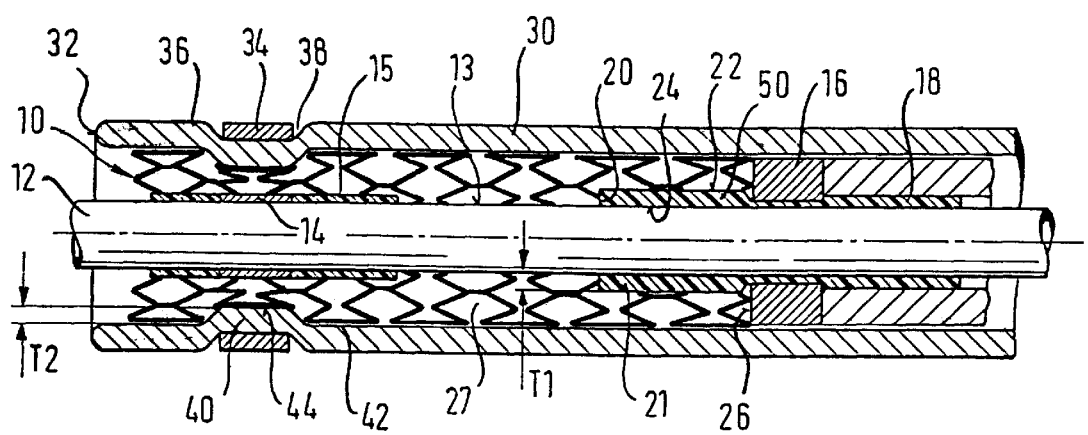
FIG. 1 is a longitudinal diametric section through the distal tip region of a delivery system for a self-expanding stent, showing the stent prior to release.

FIG. 1 shows a delivery system for a stent 10. The system is based on a tubular catheter tube 12, designed to be advanced along a guidewire (not shown). The catheter tube carries on its cylindrical surface 13 a distal marker 14, retained axially in position on the tube 12 by a short length of polymeric material 15 melted onto the tube 12. A proximal marker band 16 is retained on the tube 12 in a cured annular bed 18 of polymeric adhesive. This adhesive bed extends distally of the marker band 16 as far as a distal end 20 to form a short cylindrical length 21 of the cured adhesive, distal in relation to the marker band 16, with a radially outwardly facing surface 22 and a radially inwardly facing surface 24 bonded to the cylindrical surface of the tube 12. This cylindrical zone, radially between cylindrical surfaces 22 and 24, has a radial thickness T1. Reference is made to the fact that the marker band 16 provides a distal-facing end surface 26 which defines the proximal end of a bed 27 to receive the stent 10.

Overlying the stent 10 is an outer catheter tube 30 which extends to a distal tip 32 beyond the distal end of the stent 10. Close to the distal tip 32 is a further radioactive metal marker band 34 which is swaged into the outside wall surface 36 of the outer tube 30, causing elastic deformation of the outer tube 30, locally radially inside the band 34, so that the marker band 34 sits in a ring recess 38 in the outer wall of the tube 30. This ring recess 38 has its counterpart a ring which forms a pinch zone 40 which protrudes inwardly of the inside wall 42 of the outer tube 30 by the band 34, and locally radially inside the marker band 34. This radially inwardly protruding pinch zone has a radially inside surface 44, and the radially inward extent of the pinch zone 40 between surfaces 42 and 44 is T2. It will be seen that stent 10 fits snugly around the inside surfaces 42 and 44 of the outer tube 30. One must remember that a self-expanding stent at body temperature is seeking to expand radially and so will naturally follow closely the contours of any constraining outer tube (just as it will ultimately follow closely the contours of the bodily lumen in which it is deployed).

Figure 2:
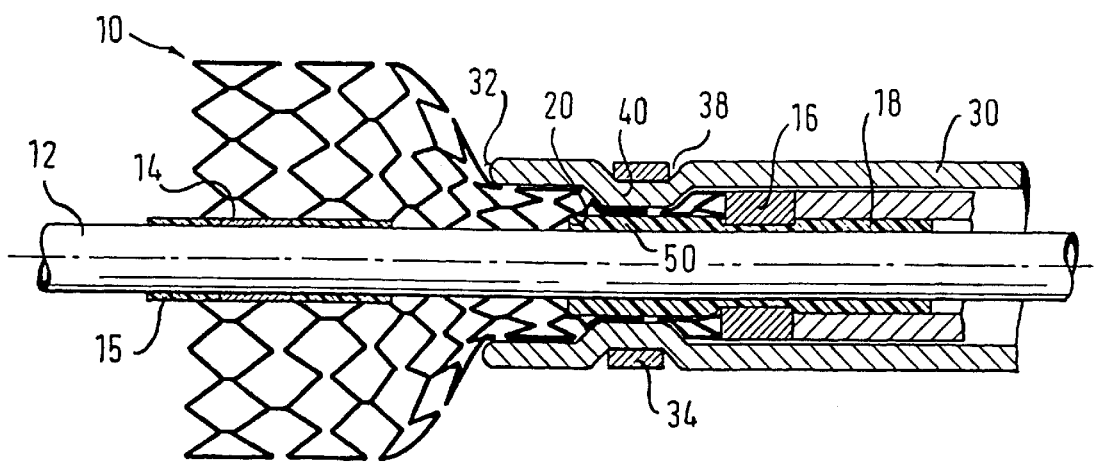
FIG. 2 is a section similar to that of FIG. 1, showing the stent partially released.

Turning now to FIG. 2, in which like elements are given the same reference numerals, one sees that the outer tube 30 has been withdrawn relative to the inner tube 12, sufficiently far to release most of the length of the stent 10, and to a point in which the first pinch zone 50 provided by the polymer between cylindrical surfaces 22 and 24 directly faces the second pinch zone 40 inside the marker band 34. It is to be noted that nowhere is the thickness of the stent 10 less than its relaxed thickness. The stents used by applicant are made of Nitinol memory metal and so, in the context of the present invention, substantially incompressible. It must be noted, however, that there is spacing shown in FIG. 1, between the stent and the surfaces radially inside it, corresponding to the reality that the stent has expanded as much as it is permitted to expand, at all times. Note further that in FIG. 2 there appears to be no gap between the stent 10 and the first pinch zone 50, but only in the part of the length of the stent which lies radially directly inside the second pinch zone 40. Proximally of pinch zone 40 at the very distal end of the stent 10, there is still a spacing between the stent 10 and the first pinch zone 50. However, with a further withdrawal movement of the outer tube 30, bringing the second pinch zone 40 to the proximal end of the first pinch zone 50, this gap will disappear.

Continued proximal withdrawal of the outer tube 30 will carry the pinch zone 40 proximally beyond pinch zone 50, at which point the stent 10 will be able to ease out of the proximal end of its bed. By that point, such a large proportion of the length of the stent will have taken up position on the bodily lumen wall that any out of control springing or jumping of the stent, and uncontrolled axial movement of the stent relative to the bed, will be either eliminated altogether or reduced to an acceptably minuscule level.

As with conventional delivery systems, withdrawal of the outer sheath past the proximal end of the stent deploys the self-expanding stent fully, and allows the delivery system to be retracted from the patients body.

What is shown in the drawings represents what for the applicant at the present time is the best mode of putting the invention into effect. However, readers will appreciate that a wealth of variations is possible for those skilled in the art.

Those skilled in the art will be familiar with the materials with which self-expanding stents are constructed, and with the materials with which delivery systems for such stents are constructed. Those skilled in the art are familiar with assembly techniques for achieving the required degrees of flexibility, pushability, column strength and torquability in stent delivery systems.

As mentioned above, there is scope for profiling the first and second pinch zones, other than as shown in the drawings, in order to achieve the desired profiles of withdrawal force, and further refine the degree of control over the release of self-expanding stents from such delivery systems. There is also, naturally, much scope for refining the design and provision of marker bands, and for coordinating the distribution of marker bands and pinch zones to achieve synergistic effects.

What is claimed is:

1. A delivery catheter for a self-expanding stent having proximal and distal ends, the catheter having proximal and distal ends, comprising:

an inner member having a bed with a radially outward facing surface, the bed being disposed at or near the distal end of the catheter;

an outer catheter tube circumferentially surrounding the bed; and the outer tube being arranged to be withdrawn proximally to release a self-expanding stent contained in the outer catheter tube radially outwardly;

the bed surface defining a first pinch zone;

a second pinch zone defined on the radially inwardly facing surface of the outer tube;

the first and second pinch zones facing each other when the distal end of the outer tube is not quite fully withdrawn proximally, relative to the bed;

the facing first and second pinch zones defining a reduced-width annulus for pinching a proximal end of the stent to make available increased resistance to relative axial movement between the stent and the catheter just prior to full withdrawal of the outer tube.

2. A delivery catheter as claimed in claim 1, wherein the outer tube is a full length outer catheter tube.

3. A delivery catheter as claimed in claim 1, wherein the outer tube carries a marker.

4. A delivery catheter as claimed in claim 3, wherein the outer tube marker deforms the outer tube radially inwardly to create the second pinch zone.

5. A delivery catheter as claimed in claim 1, in which the first pinch zone is formed by an annulus of cured polymer.

6. A delivery catheter as claimed in claim 5, wherein the cured polymer is placed around a catheter marker.

7. A delivery catheter as claimed in claim 6, wherein the catheter marker also serves to define the proximal end of the stent bed.

8. A stent delivery catheter as defined in claim 1, further in combination with a self-expanding stent contained within a distal region of the outer catheter tube.

9. A delivery catheter as defined in claim 8 wherein the proximal end of the stent is disposed about the first pinch zone.

10. An apparatus as claimed in claim 1 further comprising, in combination, a self-expanding stent contained within the outer catheter tube, the stent having a proximal end disposed about the bed of the inner member.

11. An apparatus as claimed in claim 2 further comprising, in combination, a self-expanding stent contained with the outer catheter tube, the stent having a proximal end disposed about the bed of the inner member.

12. An apparatus as claimed in claim 3 further comprising, in combination, a self-expanding stent contained within the outer catheter tube, the stent having a proximal end disposed about the bed of the inner member.

13. An apparatus as claimed in claim 4 further comprising, in combination, a self-expanding stent contained within the outer catheter tube, the stent having a proximal end disposed about the bed of the inner member.

14. An apparatus as claimed in claim 5 further comprising, in combination, a self-expanding stent contained within the outer catheter tube, the stent having a proximal end disposed about the bed of the inner member.

15. An apparatus as claimed in claim 6 further comprising, in combination, a self-expanding stent contained within the outer catheter tube, the stent having a proximal end disposed about the bed of the inner member.

16. An apparatus as claimed in claim 7 further comprising, in combination, a self-expanding stent contained within the outer catheter tube, the stent having a proximal end disposed about the bed of the inner member.

17. An apparatus as claimed in claim 8 further comprising, in combination, a self-expanding stent contained within the outer catheter tube, the stent having a proximal end disposed about the bed of the inner member.

18. An apparatus as claimed in claim 9 further comprising, in combination, a self-expanding stent contained within the outer catheter tube, the stent having a proximal end disposed about the bed of the inner member.

* * * * *